United States Patent
Fischer et al.

(10) Patent No.: US 11,007,506 B2
(45) Date of Patent: May 18, 2021

(54) METHOD FOR PREPARING MIXED METAL OXIDE CATALYSTS CONTAINING MOLYBDENUM AND BISMUTH

(71) Applicant: Evonik Operations GmbH, Essen (DE)

(72) Inventors: Achim Fischer, Goldbach (DE); Axel Mescher, Hattingen (DE); Harald Jakob, Hasselroth (DE)

(73) Assignee: Evonik Operations GmbH, Essen (DE)

( * ) Notice: Subject to any disclaimer, the term of this patent is extended or adjusted under 35 U.S.C. 154(b) by 544 days.

(21) Appl. No.: 15/742,576

(22) PCT Filed: Jul. 19, 2016

(86) PCT No.: PCT/EP2016/067180
§ 371 (c)(1),
(2) Date: Jan. 8, 2018

(87) PCT Pub. No.: WO2017/013115
PCT Pub. Date: Jan. 26, 2017

(65) Prior Publication Data
US 2018/0207617 A1    Jul. 26, 2018

(30) Foreign Application Priority Data

Jul. 20, 2015  (EP) .................................. 15177519

(51) Int. Cl.
| | |
|---|---|
| *B01J 23/00* | (2006.01) |
| *B01J 37/00* | (2006.01) |
| *C07C 45/35* | (2006.01) |
| *B01J 23/887* | (2006.01) |
| *B01J 27/192* | (2006.01) |

(Continued)

(52) U.S. Cl.
CPC ......... *B01J 23/002* (2013.01); *B01J 23/8876* (2013.01); *B01J 23/8898* (2013.01); *B01J 27/192* (2013.01); *B01J 35/023* (2013.01); *B01J 35/08* (2013.01); *B01J 37/0018* (2013.01); *B01J 37/0045* (2013.01); *B01J 37/06* (2013.01); *B01J 37/086* (2013.01); *B01J 37/088* (2013.01); *C07C 45/35* (2013.01); *C07C 51/252* (2013.01); *B01J 23/8933* (2013.01); *B01J 2523/00* (2013.01); *B01J 2523/18* (2013.01); *B01J 2523/19* (2013.01); *B01J 2523/31* (2013.01); *B01J 2523/3706* (2013.01); *B01J 2523/3712* (2013.01); *B01J 2523/47* (2013.01); *B01J 2523/48* (2013.01); *B01J 2523/51* (2013.01); *B01J 2523/54* (2013.01); *B01J 2523/55* (2013.01); *B01J 2523/56* (2013.01); *B01J 2523/63* (2013.01); *B01J 2523/67* (2013.01); *B01J 2523/68* (2013.01); *B01J 2523/69* (2013.01); *B01J 2523/72* (2013.01); *B01J 2523/824* (2013.01); *B01J 2523/828* (2013.01); *B01J 2523/84* (2013.01)

(58) Field of Classification Search
CPC .. B01J 23/002; B01J 23/8876; B01J 23/8898; B01J 27/192; B01J 35/023; B01J 35/08; B01J 37/0018; B01J 37/0045; B01J 37/06; B01J 37/086; B01J 37/088; C07C 45/35; C07C 51/252
See application file for complete search history.

(56) References Cited

U.S. PATENT DOCUMENTS

| | | | | |
|---|---|---|---|---|
| 3,044,965 A | * | 7/1962 | Callahan .................. | B01J 23/18 502/212 |
| 2004/0034249 A1 | * | 2/2004 | Arnold ..................... | B01J 37/08 562/547 |

(Continued)

FOREIGN PATENT DOCUMENTS

| | | |
|---|---|---|
| CN | 101164694 A | 4/2008 |
| CN | 104661745 A | 5/2015 |
| DE | 102011079035 A1 | 1/2013 |

OTHER PUBLICATIONS

International Search Report and Written Opinion dated Nov. 9, 2016, in PCT/EP2016/067180, filed Jul. 19, 2016.

(Continued)

*Primary Examiner* — Sheng H Davis
*Assistant Examiner* — Michael Forrest
(74) *Attorney, Agent, or Firm* — Oblon, McClelland, Maier & Neustadt, L.L.P.

(57) ABSTRACT

The present invention relates to a process for producing mixed oxide catalysts on the basis of molybdenum and bismuth oxides in which the precursor compounds of the components of mixed oxide catalysts provided in the form of a solution and/or suspension are subjected to a spray-drying with a specific temperature regime and the spray particles obtained in this way are then calcined to yield a catalytic active mass, and to the mixed oxide catalysts obtainable by this process and to the use of these catalysts in the partial oxidation of olefins, in particular in the partial gas phase oxidation of propene to acrolein and acrylic acid. The spray drying of the precursor compounds containing solution or suspension is performed in concurrent with a gas stream having a specific entrance temperature. Alternatively, when the main gas stream has a higher entrance temperature, an additional colder gas stream can be fed in downstream. The thus obtained mixed oxide catalysts give lower a maximum temperature in the hot spot of catalyst fixed bed when they are used in the partial gas phase oxidation of olefins.

12 Claims, No Drawings

(51) Int. Cl.
*B01J 35/08* (2006.01)
*C07C 51/25* (2006.01)
*B01J 23/889* (2006.01)
*B01J 37/08* (2006.01)
*B01J 35/02* (2006.01)
*B01J 37/06* (2006.01)
*B01J 23/89* (2006.01)

(56) References Cited

U.S. PATENT DOCUMENTS

2010/0286450 A1\* 11/2010 Fischer ................ C07C 45/35 568/469.9
2011/0092734 A1\* 4/2011 Hagemeyer .......... C01G 39/006 562/598
2013/0225862 A1\* 8/2013 Tateno ................. B01J 35/0073 562/549

OTHER PUBLICATIONS

Van Well et al., "The influence of the calcination conditions on the catalytic activity of $Bi_2MoO_6$ in the selective oxidation of propylene to acrolein", Journal of Molecular Catalysis A: Chemical, vol. 256, XP 028015635. 2006, pp. 1-8.
Le et al., "Bismuth molybdate catalysts synthesized using spray drying for the selective oxidation of propylene", Applied Catalysis A: General, vol. 249, XP 004447831, 2003, pp. 355-364.
U.S. Pat. No. 8,008,227, Aug. 30, 2011, 2009/0030230, Fischer et al.
U.S. Appl. No. 12/107,343, filed Jan. 5, 2017, 2017/0001532, Taniguchi.
U.S. Appl. No. 12/528,407, filed Dec. 23, 2010, 2010/0324331, Fischer et al.
U.S. Appl. No. 13/491,753, filed Nov. 8, 2012, 2012/0283088, Fischer et al.

\* cited by examiner

METHOD FOR PREPARING MIXED METAL OXIDE CATALYSTS CONTAINING MOLYBDENUM AND BISMUTH

The present invention relates to a process for producing mixed oxide catalysts, to the mixed oxide catalysts obtainable by this process and to the use of these catalysts in the partial oxidation of olefins.

Mixed oxide catalysts, especially those based on molybdenum oxides and bismuth oxides, are used in the industrial preparation of acrolein and acrylic acid or methacrolein and methacrylic acid, and also acrylonitrile. These compounds are prepared in the form of a heterogeneously catalysed partial oxidation of propene or of isobutene or tert-butanol with air or ammonia in the gas phase over a catalyst fixed bed containing mainly the respective mixed oxide catalyst.

In the context of the present invention, the terms "partial oxidation", "partial gas phase oxidation" and "gas phase partial oxidation" are used in such a way that they refer to conversions of organic compounds under the reactive action of molecular oxygen in which the organic compound to be oxidized partially, after the reaction has ended, contains at least one chemically bonded oxygen atom more than prior to the performance of the partial oxidation or the partial gas phase oxidation or gas phase partial oxidation.

In contrast to a partial oxidation, a partial gas phase oxidation or gas phase partial oxidation, in the context of the present invention, the term "full oxidation" is used in such a way that it refers to conversions of organic compounds under the reactive action of molecular oxygen in which all the carbon atoms present in the organic compounds are converted to oxides of carbon and/or all the hydrogen atoms present in the organic compounds to oxides of hydrogen.

The energy required to start the oxidation reaction is supplied to the reaction via an external heating medium, on the industrial scale, for example, via a salt bath surrounding the reaction tubes which contain the mixed oxide catalyst and through which the reaction gases flow. After the oxidation reaction has started, the external heating medium generally serves to remove the heat of reaction formed, since gas phase partial oxidations typically proceed exothermically. Commercial mixed oxide catalysts typically have service lives of several years. Within this time, the catalyst has aged, meaning that it no longer has the same activity as at the start of its use in the reaction, and it is then necessary to exchange the spent catalyst bed for fresh catalyst.

This ageing is observed especially in the case of use of mixed oxide catalysts having an active mass containing molybdenum in the oxidized state, in the performance of partial gas phase oxidations in the presence of water or steam. In most cases, the steam is formed in the partial gas phase oxidation. It is believed that the steam present in the partial gas phase oxidation forms $MoO_2(OH)_2$, which is volatile, with the molybdenum present in the catalyst fixed bed in the oxidized state. The specialist literature therefore takes the view that, during the long-term operation of a heterogeneously catalysed partial gas phase oxidation, molybdenum sublimes continuously out of the active mass of the mixed oxide catalyst as $MoO_2(OH)_2$ (cf. Investigations of the mechanism and kinetics leading to a loss of molybdenum from bismuth molybdate catalysts, L. Zhang et al., Applied Catalysis A: General (1994), 117, 163-171). The loss of the active molybdenum component in mixed oxide catalysts is at its most marked particularly in the region of what are called the hotspots in the catalyst fixed bed. A hotspot is generally understood by a person skilled in the art of heterogeneous catalysis to mean the region of a catalyst fixed bed in which the evolution of heat in the reaction that proceeds over the catalyst fixed bed is at its strongest in flow direction of the gaseous reaction mixture. A catalyst fixed bed may have a plurality of hotspots. After passing through these regions, the temperature in flow direction of the gases also falls significantly, such that molybdenum oxide is precipitated again as a thin coating or film at the colder points on the inner wall of the reaction tube (cf. EP 2 155 376 A1).

Once a region of the fixed catalyst bed has been subject to bleeding of molybdenum from the active component, a hotspot migrates along the catalyst fixed bed further into regions where the temperature of the catalyst fixed bed in flow direction of the gases was previously lower and which therefore have not yet been subject to bleeding of molybdenum. These regions or zones are then likewise subject to bleeding of molybdenum in a stepwise manner. Because of the zone-by-zone bleeding of the active molybdenum component from the catalyst, this process is also referred to as zone ageing (band ageing).

With increasing operating time, therefore, there is a decrease not just in the proportion of molybdenum in the active mass of the catalyst but also in the activity of the mixed oxide catalyst for the conversion to be catalysed. This is manifested in a reduced conversion of the organic reactant.

The decline in conversion can be counteracted by increasing the temperature of the salt bath required for a specific conversion to a value which, given otherwise unchanged reaction conditions, achieves the same conversion for the compound to be oxidized in a single pass through the reactor as before the decrease in the activity of the mixed oxide catalyst.

A measure of the activity of a mixed oxide catalyst or of a catalyst fixed bed containing the mixed oxide catalyst is therefore the temperature of the salt bath, surrounding the reaction tubes comprising the mixed oxide catalyst, which is required to achieve a particular conversion of the organic reactant, for example of propene or isobutene.

However, an increase in the temperature of the salt bath in order to counteract the deactivation of a molybdenum-containing mixed oxide catalyst is counterproductive for the lifetime of the mixed oxide catalyst in question. This is because higher temperatures in the catalyst bed accelerate the ageing or deactivation of the catalyst, which prematurely necessitates either the full or at least partial replacement of the spent catalyst fixed bed with fresh catalyst. This then leads to more frequent changes of the fixed catalyst bed and more frequent operation shutdowns. As well as the associated loss of production, the disposal of the spent catalyst and the production of new catalyst also constitute a considerable additional financial burden.

To solve this problem, WO 2005/049200 A1 proposes an annular unsupported catalyst produced from individual spray powders and having a cobalt/iron ratio of 2 to 4 and a cobalt/molybdenum ratio of 0.3 to 0.7. The specific ratios of cobalt to iron and of cobalt to molybdenum in combination with one another are said to lead to a lowering of the activity of the catalyst. This is said to lead to a lowering of the hotspot temperature, which has a positive effect on the long-term stability of the catalyst and the selectivity for the formation of acrolein. However, the specific ratios of catalytically active elements in the active mass considerably restrict the number of catalysts producible.

The annular mixed oxide catalyst of WO 2010/028977 A1 is also produced from two starting compositions having both different particle diameters and different compositions.

According to the technical teaching of WO 2010/028977 A1, during the production of the catalyst, it is necessary to observe a particular figure for the product of the proportions of specific particle sizes of the two starting compositions and the stoichiometric coefficient of one starting composition, in order to assure adequate stability of the catalyst. However, the associated production process is extremely complex and at the same time considerably restricts the number of catalysts producible.

A further disadvantage of the catalysts of WO 2005/049200 A1 and WO 2010/028977 A1 is that the amount of unconverted propene rises because of their reduced activity for the oxidation of propene.

The unconverted propene then has to be recycled into the partial gas phase oxidation as what is called cycle gas, which is associated with considerable capital and energy costs. In order to keep the amount of cycle gas as small as possible, therefore, in partial gas phase oxidations conducted on the industrial scale, the aim is in principle higher propene conversions than are achievable with the catalysts of WO 2005/049200 A1 or of WO 2010/028977 A1.

The published patent application EP 2 902 105 A1 also addresses the problem of molybdenum escaping from a mixed oxide catalyst. According to this document the molybdenum escapes from a composite oxide catalyst during the reaction to relatively increase the amount of vanadium in that catalyst and to excessively increase the activity to the raw material, which increases the rate of side reactions. This document teaches that the performance of the composite oxide catalysts is improved while excessive vanadium content is decreased when the composite oxide catalysts have a specific ratio of molybdenum to vanadium and a specific ratio of vanadium to antimony. EP 2 902 105 A1 further discloses the use of that composite oxide catalysts in the vapour-phase ammoxidation reaction of propane or iso-butane to yield unsaturated nitriles.

Molybdenum containing composite oxide catalysts and their use in the vapour-phase oxidation of alkanes to produce unsaturated acids or unsaturated nitriles are also disclosed in the published patent application JP 2006 055682 A1. This document teaches that the performance of the catalyst is improved when a very small amount of at least one element selected from alkaline earth metal elements and rare earth elements is added to the catalyst. Specifically, the document teaches an atomic ratio d of alkaline earth metal elements and rare earth elements to molybdenum of 0<d<0.01.

The published international patent application WO 2008/046843 A1 discloses molybdenum containing mixed oxide catalysts and their use in the vapour-phase oxidation of alkanes to yield the corresponding unsaturated aldehydes and acids. According to this document a mixed oxide catalyst should contain a very specific amount of phosphorous or cobalt in order to provide a useful selectivity for the formation of acrolein.

Accordingly, the focus of these documents is on very specific compositions of the catalysts. This, however, significantly limits the spectrum of obtainable catalysts to a rather low number of useful catalysts. Further, this also has the disadvantage that the processes for the production of catalysts are rather complicated and not to easy control.

There is therefore a need for mixed oxide catalysts which have reduced exothermicity, especially in the hotspots of a catalyst, during the performance of a partial gas phase oxidation reaction and hence are also suitable for use in industrial scale processes.

According to the invention, this problem is solved by subjecting the precursor compounds of the components of a mixed oxide catalyst provided in the form of a solution and/or suspension to a spray-drying operation with a specific temperature regime and then calcining the spray particles thus obtained to yield a catalytic active mass.

The present invention therefore provides a process for producing a mixed oxide catalyst, comprising the steps of
a) providing a solution and/or suspension of precursor compounds of components of the mixed oxide catalyst,
b) spray-drying the solution and/or suspension provided in step a) in cocurrent together with a gas stream having an entrance temperature into the spray dryer of 150+/−10° C. to 220+/−10° C. and an exit temperature from the spray dryer of 80+/−10° C. to 110+/−10° C., or
b') spray-drying the solution and/or suspension provided in step a) essentially in cocurrent together with a main gas stream having an entrance temperature into the spray dryer of 250+/−10° C. to 350+/−10° C. and an exit temperature from the spray dryer of 110+/−10° C. to 140+/−10° C., with feeding of an additional gas stream having an entrance temperature of less than 100° C. into the spray dryer between the entrance and exit points of the main gas stream into the spray dryer and from the spray dryer, and
c) calcining the spray particles obtained from step b) or b') to yield a catalytic active mass.

In the context of the present invention, a spray-drying operation is understood to mean a method of drying solutions, suspensions or pasty materials. A spray-drying operation is conducted in what is called a spray tower or spray dryer in which there is a spray device in the upper portion thereof. The spray device contains a nozzle operated by means of liquid pressure, compressed air or inert gas, or a rotating atomizer disc or rotating disc by means of which the material to be dried is introduced in a hot gas stream that dries it within fractions of a second to give a fine powder. In order that the powders obtained from the spray-drying can be converted to the mixed oxide catalyst in a subsequent calcination, it has to be ensured that the components of the catalyst to be produced that are present in the precursor compounds of the spray powder are not reduced. Therefore, in the spray-drying according to the invention, an oxygen-containing gas, especially air, oxygen-enriched air or even pure oxygen is used as hot gas. For reasons of cost, preference is given to simply using air. In the process according to the invention, the hot gas flows either in the direction of the jet with which the solution and/or suspension is sprayed into the spray tower, i.e. in cocurrent, or the hot gas flows partly in the direction of the spray jet and additional hot gas flows into the spray jet from a point in the wall of the spray dryer. Spray-drying of a solution and/or suspension in cocurrent together with a gas stream, in the context of the present invention, is understood to mean a spray-drying operation in which the hot gas flows in the direction of the jet with which the solution and/or suspension is sprayed into the spray tower A spray-drying operation of a solution and/or suspension essentially in cocurrent together with a main gas stream, in the context of the present invention, is understood to mean a spray-drying operation in which the predominant proportion of the hot gas flows in the direction of the jet with which the solution and/or suspension is sprayed into the spray tower, and additional gas in a smaller amount than the main gas stream is supplied to the spray dryer at a point between the entrance and exit points for the main gas stream into the spray dryer. The dry material obtained is usually separated from the air stream by a cyclone separator in the lower portion of the spray dryer and can be removed at that point. Spray dryers can be operated continuously or batchwise.

In the context of the present invention, the term cocurrent is used synonymous with parallel flow or direct current mode and means that the gas stream and the solution and/or suspension sprayed in flow in the same direction. By comparison, a mode where the gas stream flows exclusively or essentially in the opposite direction of the solution and/or suspension to be dried is considered as countercurrent in the context of the present invention.

In the context of the present invention, it has been found that both the direction in which the hot gas flows through the spray dryer and the entrance and exit temperatures of the hot gas have an influence on the mixed oxide catalyst produced. For example, the direction with which the hot gas flows through the spray dryer has an influence on the size of the spray particles. A spray-drying operation in which the hot gas flows through the spray dryer exclusively or essentially in cocurrent with the solution and/or suspension to be dried generally generates smaller spray particles than a spray-drying operation in which the hot gas flows through the spray dryer exclusively or essentially in countercurrent to the solution and/or suspension to be dried. It has been found, more particularly, that the spray-drying with the temperature regime according to the invention generates spray particles which introduce advantageous properties into the mixed oxide catalysts produced by the process according to the invention. Thus, the mixed oxide catalysts produced by the process according to the invention, when used in the partial gas phase oxidation of olefins, lead to a lower maximum temperature, especially in the hotspot of the catalyst fixed bed, than comparative catalysts which have been subjected to a spray-drying operation different from that according to the invention in their preparation. Because of the reduced maximum temperature in the case of use in the partial gas phase oxidation of olefins, the mixed oxide catalysts produced by the process according to the invention are subjected to lower heat stress, which slows ageing and particularly zone ageing of the catalyst.

In the case of use of conventional mixed oxide catalysts in the heterogeneously catalysed partial gas phase oxidation of olefins, the catalyst fixed bed is typically diluted with inert materials. This is because the dilution of the catalyst fixed bed reduces both the concentration of the catalyst used and the activity thereof for the partial gas phase oxidation in question, which simultaneously also leads to lowering of the maximum temperature of the catalyst in the oxidation. However, a dilution of the catalyst fixed bed also deteriorates the conversion of olefin and the yield of the desired target compound—sometimes significantly. In contrast, the use of the mixed oxide catalysts produced by the process according to the invention allows dilution of the catalyst fixed bed with inert materials to be dispensed with. This leads to an increase in the yield of the desired oxidation product. For reactions in which dilution of the catalyst fixed bed with inert materials is nevertheless beneficial or even unavoidable, the use of the catalysts produced by the process according to the invention allows targeted and well-dosed use of inert materials. This makes it possible to work with smaller reactor volumes than those that are conventional. In particular, however, this reduces the activity of the fixed catalyst bed for the partial gas phase oxidation in question to a lesser degree than in conventional processes. Dispensing with inert materials or at least the reduced use of inert materials in the fixed catalyst bed therefore increases the economic attractiveness of a corresponding process for partial gas phase oxidation.

The process according to the invention therefore allows the properties of the final catalyst to be influenced at quite an early stage in the catalyst production.

The precursor compounds which are provided with a solution and/or suspension in step a) of the process according to the invention serve as a source of the elemental constituents of the desired mixed oxide. Sources of the elemental constituents of the mixed oxide are compounds that are already in the form of oxides and/or are convertible to oxides by heating, preferably in the presence of molecular oxygen and/or oxygen-containing oxidizing agents.

Suitable compounds convertible to oxides are especially those compounds which, aside from the oxides, do not leave behind any further solids but can be broken down and/or decomposed proportionally to compounds that escape entirely in gaseous form. These are particularly nitrates, formates, oxalates, acetates, carbonates, organic amine compounds, ammonium salts and/or hydroxides.

In the case of use of precursor compounds that are already in the form of oxides, for example samarium oxide, it is appropriate to add an acid or a base, preferably an acid, in order to dissolve the oxide or at least improve its solubility or suspendability in water. If the acid or base in question is not broken down and/or decomposed to compounds that escape entirely in gaseous form in the course of heating and especially in the course of calcining, additional incorporation of specific elements into the mixed oxide can be effected via addition of acid or base.

With regard to the elements or components which are introduced into the desired mixed oxides via the precursor compounds, the process according to the invention is not subject to any restrictions. Rather, the elemental constituents of the desired mixed oxide that are provided via the corresponding precursor compounds in step a) are defined via the stoichiometry of the desired mixed oxide both in terms of their selection and in terms of the amount thereof used. The stoichiometry of the mixed oxide catalyst or of the mixed oxide present in the catalyst rather depends on the uses for which it is intended.

The mixed oxide catalysts used in partial oxidation of olefins contain molybdates of a wide variety of different types. Among these, bismuth molybdates are typically the most common. If the mixed oxide catalysts produced by the process according to the invention are to be used in the partial oxidation of olefins, the solution or suspension provided in step a) necessarily contains a precursor compound of bismuth and a precursor compound of molybdenum or a precursor compound containing both bismuth and molybdenum. A suitable source of bismuth is, for example, bismuth nitrate, and a suitable source of molybdenum is ammonium heptamolybdate. In addition, a solution and/or suspension provided in step a) also contains at least one precursor compound of elements selected from the group consisting of iron, tungsten, phosphorus, cobalt, nickel, alkali metal, alkaline earth metal, cerium, manganese, chromium, vanadium, niobium, selenium, tellurium, gadolinium, lanthanum, yttrium, palladium, platinum, ruthenium, silver, gold, samarium, silicon, aluminium, titanium and zirconium. Preferably, the solution and/or suspension provided in step a) contains precursor compounds of the elements bismuth, molybdenum, iron, cobalt, nickel, manganese, potassium, phosphorus, samarium and silicon.

A solution and/or suspension provided in step a) is typically prepared by dissolving or suspending the individual precursor compounds of the elements or components in question in a liquid medium which has to be suitable for use in the spray-drying. Because of this requirement, it is preferable to use water as solvent in the preparation of the solution or suspension. In addition, it is possible to add acids of the salts used to a solution of corresponding precursor compounds for better dissolution thereof, for example nitric acid, phosphoric acid or carbonic acid.

In the context of the present invention, a suspension provided in step a) is preferably prepared by the following method:

First of all, a solution I is prepared by first dissolving the nitrates of iron, cobalt, nickel, manganese and potassium in water, heating the solution obtained, preferably heating to 50° C., and adding an aqueous solution of an Sm(III) source. The Sm(III) source may be samarium(III) nitrate or samarium(III) oxide, preference being given to adding nitric acid in the case of samarium(III) oxide for dissolution of the oxide.

For a solution II, a molybdate source, preferably ammonium heptamolybdate, is dissolved in heated water, preferably heated to 50° C., and then phosphoric acid is added.

In addition, a further solution III is prepared from bismuth nitrate and nitric acid.

The solution II is provided and the solution III is added gradually to this solution while stirring to yield a new mixture. By adding the solution I to this mixture, a precipitate containing the mixed components for the production of the active mass of the catalysts is obtained.

The suspension containing the precipitate can be fed directly to the spray-drying. Optionally, it is also possible to separate the precipitate from the suspension, to suspend it in another liquid medium and/or to bring the precipitate into solution by adding acids.

If a suspension is subjected to the spray-drying in the process according to the invention, the concentration of the solids in this suspension is 10% to 50% by weight, preferably 20% to 40% by weight, based on the total mass of the suspension.

By means of a pump, the solution and/or suspension is fed into the spray tower for spraying from a reservoir of the rotating atomizer disc. The throughput of the solution and/or suspension which is sprayed into the spray tower in this way is 1 to 6 kg/h, preferably 1.5 to 5.5 kg/h. The speed of rotation of the rotating atomizer disc is within a range from 30 000 rpm+/−10% to 50 000 rpm+/−10%, preferably 45 000 rpm+/−10% (rounds per minute).

In the context of the present invention, it has been found that a spray-drying operation conducted in cocurrent with a gas entrance temperature of 160+/−10° C. to 200+/−10° C. into the spray dryer and a gas exit temperature of 90+/−10° C. to 105+/−10° C. from the spray dryer enables the production of mixed oxide catalysts having a maximum temperature nearly 20° C. lower in the partial gas phase oxidation of olefins, especially of propene. In addition, in the context of the present invention, it has likewise been found that a spray-drying operation conducted essentially in cocurrent with an entrance temperature of the main gas stream of 260+/−10° C. to 300+/−10° C. into the spray dryer and an exit temperature of 115+/−10° C. to 130+/−10° C. from the spray dryer enables the production of mixed oxide catalysts having a maximum temperature nearly 15° C. lower in the partial gas phase oxidation of olefins, especially of propene.

In one embodiment of the process according to the invention, therefore, in step b), the gas stream has an entrance temperature of 160+/−10° C. to 200+/−10° C. into the spray dryer and an exit temperature from the spray dryer of 90+/−10° C. to 105+/−10° C. Preferably, in step b) of the process according to the invention, the gas stream has an entrance temperature of 180+/−10° C. to 200+/−10° C. into the spray dryer and an exit temperature of 90+/−10° C. to 105+/−10° C. from the spray dryer.

In addition, it has been found that the spray particles generated in accordance with the invention introduce advantageous properties into the final mixed oxide catalysts especially when the residual moisture content of the spray particles is less than 20%, but at least 8%. Spray particles of this kind are obtained particularly in the case of use of specific volume flow rates of the hot gas for the spray-drying in step b) or b') of the process according to the invention. The volume flow rate correlates with the mean flow rate via the relationship $$Q = v_a \cdot A \text{ with}$$

Q: volume flow rate in $m^3/s$,
$v_a$: mean flow rate over the cross section in m/s, and
A: cross-sectional area at the site in $m^2$.

In the context of the present invention, catalysts having advantageous properties are obtained at a mean flow rate of the gas stream in the spray dryer of 2.0+/−0.3 cm/s to 4.5+/−0.3 cm/s in step b) of the process according to the invention, and at a mean flow rate of the main gas stream in the spray dryer of 2.0+/−0.3 cm/s to 4.5+/−0.3 cm/s in step b') of the process according to the invention. These flow rates correspond to a volume flow rate of about 40+/−5 $Nm^3/h$ to about 80+/−5 $Nm^3/h$ in step b) or b') of the process according to the invention when a spray dryer having a cylindrical drying region of length 0.62 m and diameter 0.8 m is used, for example a rotary disc spray tower of the Mobile Minor™ type from GEA Niro. The figure for the volume in standard cubic metres ($Nm^3$) refers to the volume in cubic metres that the particular gas used for spray-drying has under standard conditions, i.e. at 25° C. and 1 bar, also referred to as standard temperature and pressure.

In a further embodiment of the process according to the invention, the gas stream in step b) therefore has a mean flow velocity in the spray dryer of 2.0+/−0.3 cm/s to 4.5+/−0.3 cm/s.

Preferably, the gas stream in step b) has a mean flow velocity in the spray dryer of 2.5+/−0.3 cm/s to 4.2+/−0.3 cm/s, especially of 2.8+/−0.3 cm/s to 4.0+/−0.3 cm/s. These flow rates correspond to a volume flow rate of about 45+/−5 $Nm^3/h$ to about 75+/−5 $Nm^3/h$ or of about 51+/−5 $Nm^3/h$ to about 71+/−5 $Nm^3/h$ when a spray dryer having a cylindrical drying region of length 0.62 m and diameter 0.8 m is used.

In an alternative embodiment of the process according to the invention, the main gas stream in step b') has an entrance temperature into the spray dryer of 260+/−10° C. to 300+/−10° C. and an exit temperature from the spray dryer of 115+/−10° C. to 130+/−10° C. Preferably, the main gas stream in step b') has an entrance temperature into the spray dryer of 270+/−10° C. to 290+/−10° C. and an exit temperature from the spray dryer of 115+/−10° C. to 130+/−10° C.

In a further alternative embodiment of the process according to the invention, in step b'), an additional gas stream having an entrance temperature of not more than 30° C. is fed into the spray dryer.

In a further alternative embodiment of the process according to the invention, the main gas stream in step b') has a mean flow velocity in the spray dryer of 2.0+/−0.3 cm/s to 4.5+/−0.3 cm/s. These flow rates correspond to a volume flow rate of about 40+/−5 $Nm^3/h$ to about 80+/−5 $Nm^3/h$ when a spray dryer having a cylindrical drying region of length 0.62 m and diameter 0.8 m is used.

Preferably, the main gas stream in step b') has a mean flow velocity in the spray dryer of 2.5+/−0.3 cm/s to 3.5+/−0.3 cm/s, especially of 2.8+/−0.3 cm/s. These flow rates correspond to a volume flow rate of about 50+/−5 Nm³/h to about 60+/−5 Nm³/h or about 51+/−5 Nm³/h when a spray dryer having a cylindrical drying region of length 0.62 m and diameter 0.8 m is used.

In an additional alternative embodiment of the process according to the invention, the additional gas stream in step b') has a mean flow velocity of less than 2.0 cm/s. This flow rate corresponds to a volume flow rate of about 35 Nm³/h when a spray dryer having a cylindrical drying region of length 0.62 m and diameter 0.8 m is used. Preferably, the additional gas in step b') has a mean flow velocity of not more than 1.5+/−0.3 cm/s and especially a flow rate of 1.0+/−0.3 cm/s. These flow rates correspond to a volume flow rate of about 27 Nm³/h or about 20+/−5 Nm³/h when a spray dryer having a cylindrical drying region of length 0.62 m and diameter 0.8 m is used.

With regard to the direction, relative to the wall of the spray dryer, at which the additional gas stream enters the spray dryer, the process according to the invention is not subject to any restrictions in principle. Therefore, the additional gas stream can enter the spray dryer in cocurrent, in countercurrent, at right angles to the main gas stream or in mixtures or superimpositions of these directions. Good results are achieved in the context of the process according to the invention when the additional gas stream is fed in at an angle of 90+/−5° to 0° relative to the wall of the spray dryer in the upward direction, towards the upper end of the spray dryer, in the direction of the axis of the spray dryer. If the angle of the additional gas stream is more than 90° relative to the wall of the spray dryer, the additional gas stream points slightly downward, toward the lower end of the spray dryer, in the direction of the axis of the spray dryer. Deviations of this kind from an upward direction pointing toward the upper end of the spray dryer, in the context of the present invention, are error tolerances due to vortices resulting from the main gas stream and the like. In addition, it is also possible in the context of the present invention to tilt the angle of the additional gas stream relative to the axis of the spray dryer as well. When the solution and/or suspension sprayed into the spray dryer with a rotary spraying disc describes a screw-shaped downward motion within the spray dryer, in one embodiment, the angle of the additional gas stream is tilted away from the axis of the spray dryer in such a way that the additional gas stream points in the direction from which the solution and/or suspension sprayed into the spray dryer comes. In an alternative embodiment, the angle of the additional gas stream is tilted away from the axis of the spray dryer such that the additional gas stream points in the direction in which the solution and/or suspension sprayed into the spray dryer moves through the spray-drying operation.

In one embodiment of the process according to the invention, therefore, the additional gas stream in step b') is fed in at an angle of 90+/−5° to 0° relative to the wall of the spray dryer upward in the direction of the axis of the spray dryer.

Preferably, the additional gas stream in step b') is fed in at an angle of 90° to 0°, especially at an angle of 90° or 0° and more preferably at an angle of 90° relative to the wall of the spray dryer upward in the direction of the axis of the spray dryer.

With regard to the entry point of the additional gas into the spray dryer too, the process according to the invention is not subject to any restrictions. In order, however, to achieve very substantial homogeneity of mixing of the main gas stream with the stream of the additional gas, the additional gas stream is preferably fed into the spray dryer at a point between one third and three quarters of the distance between the entrance and exit points for the main gas stream in the spray dryer. In this way, the entire volume of the spray dryer available for the spray-drying is divided into two zones having easily regulatable temperature gradients. Preferably, the additional gas stream is fed into the spray dryer at a point at half the distance between the entry point and the exit point of the main gas stream in the spray dryer. As a result, the entire volume of the spray dryer available for the spray-drying is divided into two zones of equal size having easily regulatable temperature gradients.

In another embodiment, therefore, in step b'), the additional gas stream is fed into the spray dryer at a point between one third and three quarters of the distance between the entrance and exit point for the main gas stream in the spray dryer.

The solution and/or suspension provided in step a) of the process according to the invention may already comprise precursor compounds of all the components of the mixed oxide catalyst. This allows the production of mixed oxide catalysts directly from a homogeneous spray powder. In contrast, mixed oxide catalysts, especially those for the oxidation of olefins, according to the processes of WO 2005/049200 A1 and WO 2010/028977 A1, are typically produced from two spray powders each having different particle size distribution. In comparison to these processes, the process according to the invention constitutes a distinct process simplification.

If the catalytic active mass for a mixed oxide catalyst is produced batchwise with just a single layer of catalytic active mass, the steps of the process according to the invention are conducted as frequently as needed for production of the required amount of catalytic active mass.

In a further embodiment of the process according to the invention, therefore, the solution and/or suspension provided in step a) comprises precursor compounds of all components of the mixed oxide catalyst.

Alternatively, it is of course also additionally possible that the solutions and/or suspensions provided in step a) each comprise precursor compounds of different components of the mixed oxide catalyst. This enables, for example, the production of shell catalysts having layers of different compositions. In that case, in individual spray-drying operations, spray particles are first produced from different solutions in each case, and the spray particles thus obtained are calcined individually on their own and then applied to a support as individual layers one on top of another. For example, in this way, a shell catalyst having layers of different activities can be produced for the reaction to be catalysed.

In an alternative embodiment of the process according to the invention, solutions and/or suspensions comprising precursor compounds each of different components of the mixed oxide catalyst are used in step a), and steps a) and b) or a) and b') are repeated more than once.

In very few cases does the mixed oxide catalyst obtained after the calcination constitute the catalyst actually used in the partial gas phase oxidation. Rather, the pulverulent catalyst obtained from the calcination is subjected to a shaping step which yields the actual catalyst.

In a further embodiment, the process according to the invention therefore additionally comprises the steps of d) optionally mixing the catalytic active masses obtained from step c), if solutions and/or suspensions of precursor compounds each of different components of the mixed oxide catalyst are used in step b) or b'), to yield a catalytic active mass comprising all the components of the mixed oxide catalyst, e) adding a shaping agent and/or binder to the catalytic active mass obtained from step c) or d), f) shaping the catalytic active mass obtained from step e) to obtain a shaped body comprising the mixed oxide catalyst, and g) drying and/or calcining and/or heat-treating the shaped catalyst body obtained from step f).

By a drying operation, which typically takes place at temperatures of more than 100° C., any residual moisture still present in the shaped body obtained from step f) is removed. The calcining, which is typically conducted at temperatures of about 430° C. or more, serves to remove or burn off added shaping agents and/or binders from the shaped body. In addition, another calcining operation in the production process ensures that those components of the mixed oxide catalyst that are still in the form of the precursor compounds are ultimately converted to the corresponding oxides. In a shaping operation of the pulverulent catalytic active mass, the catalyst should preferably be thermally after-treated within the temperature range from 450 to 600° C., in order that the active mass has solidified sufficiently for later use in industrial reactors or to any degree. This is generally effected by a final heat treatment.

For industrial use, it is particularly appropriate, after addition of commercial shaping agents and binders, to shape the pulverulent catalytic active mass. This can be accomplished by tableting or extrusion or by coating of a support. With respect to its geometric shape, the support is not limited to specific shapes or to a particular number of shapes. Rather, the geometric shape of the support depends on the specifications of the reactor (e.g. tube diameter, length of catalyst bed, etc.). For example, the support may take the form of a cylinder, a ball, a pyramid, a saddle or a polyhedron, but may also be a wall of a reaction space. Preferably, the support has the shape of a ball.

Binders used may be various oils, cellulose derivatives, polyvinyl alcohols, saccharides, acrylates and the alkyl derivatives thereof, mixtures or condensates thereof. Preference is given to using acrylates, polyvinyl alcohols and cellulose derivatives, and particular preference to using derivatives and condensates of acrylates and/or celluloses and mixtures thereof.

Alternatively, it is also possible to use the catalytic active mass obtained from step c) to produce what is called a washcoat suspension, to apply the latter to a support material and to convert the coated support material to a supported mixed oxide catalyst by drying and/or calcining. In the context of the present invention, therefore, a washcoat suspension refers to any kind of suspension comprising a catalytic active mass obtained or obtainable by the process according to the invention.

In an alternative embodiment, the process according to the invention therefore additionally comprises the steps of h) providing a washcoat suspension comprising the catalytic active mass obtained from step c), i) applying the washcoat suspension from step h) to a support material, and j) drying and/or calcining and/or heat-treating the support material obtained from step i) to yield a supported mixed oxide catalyst.

Preferably, commercial shaping agents and binders as described above are added to the washcoat suspension in step h) in order to facilitate or to enable fixing of the pulverulent catalytic active mass on the support material.

In this alternative embodiment of the process according to the invention too, the support, in terms of its geometric shape, is not limited to specific shapes or to a particular number of shapes. Rather, the geometric shape of the support depends on the specifications of the reactor (e.g. tube diameter, length of catalyst bed, etc.). For example, the support may take the form of a cylinder, a ball, a pyramid, a saddle or a polyhedron, but may also be a wall of a reaction space. Preferably, the support has the shape of a ball.

In addition, the present invention also provides a washcoat suspension comprising a catalytic active mass obtained or obtainable by the process according to the invention.

To produce the washcoat suspension according to the invention, a catalytic active mass obtained or obtainable by the process according to the invention is suspended in deionized water. If required, the washcoat suspension thus obtained is subjected to a treatment with a dispersing unit in order to assure homogeneous particle distribution in the suspension. Subsequently, a binder, as described above, is added to the washcoat suspension.

In the simplest case, the application of a washcoat suspension according to the invention to a support material is effected by spray application of the washcoat suspension. Preferably, the application of the washcoat suspension is conducted in such a way that the washcoat suspension provided in step h) or the washcoat suspension according to the invention is sprayed onto a bed of support bodies subjected to a circulating motion.

A suitable support body is made of a ceramic material, in particular of aluminium oxide, titanium oxide, or silicon dioxide, or silicates such as clay, kaolin, pumice, aluminium silicate and magnesium silicate, or silicon carbide and zirconium dioxide. The support body is subject to any limitations regarding its shape. Thus, it may have the form of a sphere, a ring, a pyramid, a cylinder, a saddle, or polygon or it may be the wall or attached to the wall of the reactor, in which the respective reaction is performed.

The supported mixed oxide catalyst obtained in this way comprises a support body and a shell comprising catalytically active material encasing this support body. Such supported catalysts obtained by the process according to the invention are also referred to as shell catalysts.

The mixed oxide catalysts obtained and/or obtainable by the process according to the invention are suitable for the catalysed partial gas phase oxidation of olefins to unsaturated aldehydes and/or unsaturated acids.

Preferably, the catalytic active mass or mixed oxide catalyst obtained and/or obtainable by the process according to the invention corresponds to the general formula $$(Mo_{12}Bi_aFe_b(Ni+Co)_cD_dE_eF_fG_gH_h)O_x \qquad (I)$$

where

Mo is molybdenum,

Bi is bismuth,

D is tungsten and/or phosphorus,

E is at least one of the components selected from the group consisting of lithium, potassium, sodium, rubidium, caesium, magnesium, calcium, barium and strontium, F is at least one of the components selected from the group consisting of cerium, manganese, chromium and vanadium, G is at least one of the components selected from the group consisting of niobium, selenium, tellurium, samarium, gadolinium, lanthanum, yttrium, palladium, platinum, ruthenium, silver and gold, H is at least one of the components selected from the group consisting of silicon, aluminium, titanium and zirconium, O is oxygen,
and
a=0 to 5.0
b=0.5 to 5.0
c=2 to 15
d=0.01 to 5.0
e=0.001 to 2
f=0.001 to 5
g=0 to 1.5
h=0 to 800,
and
x=a number which is determined by the valency and frequency of the components other than oxygen.

More preferably, the catalytic active mass or mixed oxide catalyst obtained and/or obtainable by the process according to the invention corresponds to the composition $(Mo_{12}Bi_{1.5}(Co+Ni)_{8.0}Fe_{1.8}Mn_{0.01}K_{0.06}P_{0.04}Si_{0.66}Sm_{0.1})O_x$.

The present invention therefore also further provides a catalytic active mass or mixed oxide catalyst obtained and/or obtainable by the process according to the invention.

The present invention therefore also further provides for the use of a mixed oxide catalyst obtained or obtainable by the process according to the invention in the preparation of unsaturated aldehydes and/or acids by partial oxidation of olefins and a process for preparing unsaturated aldehydes and/or acids by partial oxidation of olefins, in which the olefins are oxidized in the presence of a mixed oxide catalyst produced or obtainable by the process according to the invention or of a mixed oxide catalyst according to the invention.

The partial oxidation of olefins is generally conducted at temperatures of 250 to 450° C. and a pressure of 1 to 3 bara. This involves feeding the co-reactants (olefin, air or oxygen or oxygen-enriched air and inert gases) to the catalyst bed, preferably in a molar ratio of 1:6-9:3-18 at a space velocity of 2 to 10 mol of olefin per litre of catalyst bed per hour.

Preferably, the olefin is a $C_1$-$C_4$ olefin; more preferably, the olefin is propene. Propene is used for preparation of acrolein and acrylic acid particularly in chemical grade or polymer grade form, but it is also possible to use refinery grade propene. Inert gases used can be any gaseous compounds having inert behaviour under the reaction conditions described. For example, the inert gases may be nitrogen, helium, ethane, propane or mixtures thereof. It is likewise possible to circulate components unconverted in the reaction, which are removed from the product gas mixture by condensing them out.

Particularly good results are obtained in the case of use of shell and tube, plate or wall reactors; in the latter case, the catalyst is applied to the wall.

The present invention is further described by the following items:

1. Process for producing a mixed oxide catalyst, comprising the steps of
   a) providing a solution and/or suspension of precursor compounds of components of the mixed oxide catalyst,
   b) spray-drying the solution and/or suspension provided in step a) in cocurrent together with a gas stream having an entrance temperature into the spray dryer of 150+/−10° C. to 220+/−10° C. and an exit temperature from the spray dryer of 80+/−10° C. to 110+/−10° C., or
   b') spray-drying the solution and/or suspension provided in step a) essentially in cocurrent together with a main gas stream having an entrance temperature into the spray dryer of 250+/−10° C. to 350+/−10° C. and an exit temperature from the spray dryer of 110+/−10° C. to 140+/−10° C., with feeding of an additional gas stream having an entrance temperature of less than 100° C. into the spray dryer between the entrance and exit points of the main gas stream into the spray dryer and from the spray dryer, and
   c) calcining the spray particles obtained from step b) or b') to yield a catalytic active mass.

2. Process according to Item 1, wherein, in step b), the gas stream has an entrance temperature into the spray dryer of 160+/−10° C. to 200+/−10° C. and an exit temperature from the spray dryer of 90+/−10° C. to 105+/−10° C.

3. Process according to Item 1 or 2, wherein, in step b), the gas stream has a mean flow velocity in the spray dryer of 2.0+/−0.3 cm/s to 4.5+/−0.3 cm/s.

4. Process according to Item 1, wherein, in step b'), the main gas stream has an entrance temperature into the spray dryer of 260+/−10° C. to 300+/−10° C. and an exit temperature from the spray dryer of 115+/−10° C. to 130+/−10° C.

5. Process according to Item 1 or 4, wherein, in step b'), the additional gas stream is fed into the spray dryer with an entrance temperature of not more than 30° C.

6. Process according to any one of Items 1, 4 or 5, wherein, in step b'), the main gas stream has a mean flow velocity in the spray dryer of 2.0+/−0.3 cm/s to 4.5+/−0.3 cm/s.

7. Process according to any one of Items 1 or 4 to 6, wherein, in step b'), the additional gas stream has a mean flow velocity of less than 2.0 cm/s.

8. Process according to any one of Items 1 or 4 to 7, wherein, in step b'), the additional gas stream is fed in at an angle of 90+/−5° to 0° relative to the wall of the spray dryer upward in the direction of the axis of the spray dryer.

9. Process according to any one of Items 1 or 4 to 8, wherein, in step b'), the additional gas stream is fed into the spray dryer at a point between one third and three quarters of the distance between the entrance and exit points for the main gas stream in the spray dryer.

10. Process according to any one of Items 1 to 9, wherein the solution and/or suspension provided in step a) comprises precursor compounds of all components of the mixed oxide catalyst.

11. Process according to any one of Items 1 to 9, wherein solutions and/or suspensions comprising precursor compounds each of different components of the mixed oxide catalyst are used in step a) and steps a) and b) or a) and b') are repeated more than once.

12. Process according to any one of Items 1 to 11, additionally comprising the steps of
    d) optionally mixing the catalytic active mass obtained from step c), if solutions and/or suspensions of precursor compounds each of different components of the mixed oxide catalyst are used in step b) or b'), to yield a catalytic active mass comprising all the components of the mixed oxide catalyst,
    e) adding a shaping agent and/or binder to the catalytic active mass obtained from step c) or d),
    f) shaping the catalytic active mass obtained from step e) to yield a shaped body comprising the mixed oxide catalyst, and
    g) drying and/or calcining and/or heat-treating the shaped catalyst body obtained from step f).

13. Process according to any one of Items 1 to 11, additionally comprising the steps of
    h) providing a washcoat suspension comprising the catalytic active mass obtained from step c),
    i) applying the washcoat suspension from step h) to a support material, and j) drying and/or calcining and heat-treating the support material obtained from step i) to yield a supported mixed oxide catalyst.
14. Washcoat suspension comprising a catalytic active mass obtained or obtainable by a process according to any one of Items 1 to 11.
15. Catalytic active mass obtained or obtainable by a process according to any one of Items 1 to 11.
16. Catalyst obtained or obtainable by a process according to any one of Items 1 to 13.
17. Use of a mixed oxide catalyst obtained or obtainable according to any one of Items 1 to 13 in the preparation of unsaturated aldehydes and/or acids by partial oxidation of olefins.
18. Use according to Item 17, wherein the olefin is a $C_1$-$C_4$ olefin.

EXAMPLES

I. Production of Mixed Oxide Catalysts
1.1 Provision of Suspensions for Catalyst Production Example 1

A first solution (referred to hereinafter as solution I) was prepared by first dissolving the nitrates of iron, cobalt, nickel, manganese and potassium in the mass fractions of 23.2:47.26:29.28:0.0646:0.2067 in 3.5 litres of water, heating the mixture obtained to 50° C. while stirring and then adding a nitric acid solution of 0.1 mol $Sm^{3+}$ and 2 mol of $HNO_3$.

A separate second solution (referred to hereinafter as solution II) was prepared by dissolving 2118.6 g of ammonium heptamolybdate in 2.7 litres of water and then adding a solution of 4.4 g of phosphoric acid in 1 litre of water.

A further separate solution (referred to hereinafter as solution III) was prepared from 1280 g of bismuth nitrate and 0.72 mol of $HNO_3$.

Solution II was provided, and solution III was added gradually thereto, while stirring. Solution I was added to the mixture thus obtained to yield a suspension.

1.2 Production of Active Masses for the Catalysts

All the active masses for the catalysts were produced by spray-drying in a rotary disc tower of the Mobile Minor™ type (http://www.niro.com/niro/cmsdoc.nsf/WebDoc/ndkk5j9c7h) from GEA-Niro (GEA Germany, GEA Group Aktiengesellschaft, Peter-Müller-Str. 12, 40468 Dusseldorf, Germany). This spray dryer has a cylindrical section having a diameter of 0.8 m and a height of 0.62 m, in which the spray-drying is effected, and an inverted conical section that adjoins the lower end thereof and has a length of 0.72 m, which serves to collect the spray particles generated.

According to the invention, the specific particle size distribution is determined in wet dispersion by means of laser scattering according to the International Standard ISO 13320. In the context of the present invention, the particle size distribution was determined with a Particle Size Analyzer of the LS™ 13320 series and a Universal Liquid Module, both from Beckmann Coulter (Brea, Calif.), using PIDS (Polarization Intensity Differential Scattering) data. The spray particles were dispersed in ethanol and subjected to the determination of particle size distribution without ultrasound bath treatment at a relative pumping rate of about 31%. The optical model for particle size determination is the Fraunhofer model. The measurement time for the particle size determination is about 82 seconds.

The particle diameters $d_x$ reported as the measurement result are defined such that X % of the total particle volume consists of particles having a smaller diameter. This means that (100-X) % of the total particle volume consists of particles having a diameter≥$d_x$.

Example 2a (Inventive)

The suspension obtained in Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 51+/−2.5 $Nm^3$/h of air (corresponding to a mean flow rate in the spray dryer of about 2.8+/−0.3 cm/s) that had an entrance temperature into the spray dryer of 200° C. through a rotary disc having a rotation rate of 45 000 $min^{-1}$. The exit temperature of the air from the spray dryer was 105° C. The spray-dried particles obtained had a residual moisture content of 14.5%. The particle size distribution of the spray powders obtained was $d_5$=11.22 µm, $d_{10}$=13.86 µm, $d_{50}$=26.33 µm, $d_{90}$=46.39 µm and $d_{95}$=56.90 µm. The mean of the particle size distribution was 29.39 µm and the median 26.33 µm. The maximum of the particle size distribution was 28.70 µm.

Example 2b (Inventive)

The suspension obtained in Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 51+/−2.5 $Nm^3$/h of air (corresponding to a mean flow rate in the spray dryer of about 2.8+/−0.3 cm/s) that had an entrance temperature into the spray dryer of 180° C. through a rotary disc having a rotation rate of 45 000 $min^{-1}$. The exit temperature of the air from the spray dryer was 92+/−5° C. The spray-dried particles obtained had a residual moisture content of 16.4%. The particle size distribution of the spray powders obtained was $d_5$=10.74 µm, $d_{10}$=16.20 µm, $d_{50}$=33.00 µm, $d_{90}$=60.74 µm and $d_{95}$=91.39 µm. The mean of the particle size distribution was 37.99 µm and the median 33.00 µm. The maximum of the particle size distribution was 34.59 µm.

Example 2c (Inventive)

The suspension obtained in Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 71+/−2.5 $Nm^3$/h of air (corresponding to a mean flow rate in the spray dryer of about 4.0+/−0.3 cm/s) that had an entrance temperature into the spray dryer of 180° C. through a rotary disc having a rotation rate of 45 000 $min^{-1}$. The exit temperature of the air from the spray dryer was 99+/−5° C. The spray-dried particles obtained had a residual moisture content of 14%. The particle size distribution of the spray powders obtained was $d_5$=13.20 µm, $d_{10}$=16.16 µm, $d_{50}$=30.25 µm, $d_{90}$=51.33 µm and $d_{95}$=63.76 µm. The mean of the particle size distribution was 33.71 µm and the median 30.25 µm. The maximum of the particle size distribution was 31.51 µm.

Example 3a (Comparative Example)

The suspension of Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 51+/−2.5 Nm$^3$/h of air (corresponding to a mean flow rate in the spray dryer of about 2.8+/−0.3 cm/s) that had an entrance temperature into the spray dryer of 300° C. through a rotary disc having a rotation rate of 45 000 min$^{-1}$. The exit temperature of the air from the spray dryer was 180+/−5° C. The spray-dried particles obtained had a residual moisture content of 2.2%. The particle size distribution of the spray powders obtained was $d_5$=0.503 µm, $d_{10}$=6.970 µm, $d_{50}$=19.87 µm, $d_{90}$=37.10 µm and $d_{95}$=41.86 µm. The mean was 21.31 µm and the median 19.87 µm. The maximum of the particle size distribution was 19.76 µm.

Example 3b (Comparative Example)

The suspension of Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 51+/−2.5 Nm$^3$/h of air (corresponding to a mean flow rate in the spray dryer of about 2.8+/−0.3 cm/s) that had an entrance temperature into the spray dryer of 212° C. through a rotary disc having a rotation rate of 45 000 min$^{-1}$. The exit temperature of the air from the spray dryer was 120° C. The spray-dried particles obtained had a residual moisture content of 6.4%. The particle size distribution of the spray powders obtained was $d_5$=3.25 µm, $d_{10}$=10.54 µm, $d_{50}$=24.90 µm, $d_{90}$=45.86 µm and $d_{95}$=59.07 µm. The mean was 27.81 µm and the median 24.90 µm. The maximum of the particle size distribution was 28.70 µm.

Example 4a (Inventive)

The suspension from Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 51+/−2.5 Nm$^3$/h of air (corresponding to a mean flow rate in the spray dryer of about 2.8+/−0.3 cm/s) that had an entrance temperature into the spray dryer of 275° C. through a rotary disc having a rotation rate of 45 000 min$^{-1}$. Via a perpendicular feed at half the height of the drying space of the spray dryer, 20 Nm$^3$/h of additional air (corresponding to a mean flow rate in the spray dryer of about 1.0+/−0.3 cm/s) that had an entrance temperature into the spray dryer of 20° C. were sprayed into the spray dryer at an angle of 90° to the dryer wall. The exit temperature of the air from the spray dryer was 125° C., irrespective of whether it entered the spray dryer from the top downward or from the side. The spray-dried particles obtained had a residual moisture content of 11.2%. The particle size distribution of the spray powders obtained was $d_5$=9.646 µm, $d_{10}$=12.30 µm, $d_{50}$=23.00 µm, $d_{90}$=38.93 µm and $d_{95}$=44.58 µm. The mean was 24.94 µm and the median 23.00 µm. The maximum of the particle size distribution was 23.82 µm.

Example 4b (Inventive)

The suspension from Example 1 was dried in a GEA-Niro Mobile Minor™ rotary disc spray dryer: The suspension was sprayed into the spray dryer, from the top downward in cocurrent with the incoming air, at a metering rate of 2+/−0.1 l/h together with 51+/−2.5 Nm$^3$/h of air (corresponding to a mean flow rate in the spray dryer of about 2.8+/−0.3 cm/s) that had an entrance temperature into the spray dryer of 275° C. through a rotary disc having a rotation rate of 45 000 min$^{-1}$. Via a perpendicular feed at half the height of the drying space of the spray dryer, 20 Nm$^3$/h (corresponding to a mean flow rate in the spray dryer of about 1.0+/−0.3 cm/s) of additional air that had an entrance temperature into the spray dryer of 20° C. were sprayed into the spray dryer from the top downward (at an angle of 0° to the dryer wall of the spray dryer in the direction of the main air stream). The exit temperature of the air from the spray dryer was 125° C., irrespective of whether it entered the spray dryer from the top downward or from the side. The spray-dried particles obtained had a residual moisture content of 11.2%. The particle size distribution of the spray powders obtained was $d_5$=2.046 µm, $d_{10}$=8.712 µm, $d_{50}$=22.00 µm, $d_{90}$=38.66 µm and $d_{95}$=44.54 µm. The mean was 23.60 µm and the median 22.00 µm. The maximum of the particle size distribution was 38.82 µm.

1.3 Production of Catalysts from Spray-Dried Powders

Example 5

The powders produced in examples 2a to 2c, 3a to 3b and 4a to 4b were calcined in an air circulation oven at a temperature of 430+/−5° C. for a period of one hour. The mixed oxides obtained were then sprayed as an aqueous suspension onto a ceramic spherical catalyst support made of $SiO_2$ and dried at 60° C. in an air stream. The pellets thus obtained were subsequently circulated in a drum for homogenization. To solidify the active mass applied, the material obtained was also subjected to a heat treatment at a temperature of 520° C. for a period of 5 hours. All catalysts produced in this way had the composition $(Mo_{12}Bi_{1.5}(Co+Ni)_{6.0}Fe_{1.8}Mn_{0.01}K_{0.06}P_{0.04}Si_{0.66}Sm_{0.1})O_x$.

II. Testing of the Mixed Oxide Catalysts

Example 6

The catalysts produced in Example 5 from the active masses of Examples 2a to 2c and 3a to 3b were used in the partial gas phase oxidation of propene. For this purpose, a tubular reactor having an internal tube diameter of 20.5 mm was charged in each case with a catalyst fixed bed having a length of 285 cm. The tubular reactor was surrounded by a bath with which the temperature of the catalyst fixed bed and of the reaction mixture flowing through the catalyst fixed bed was regulated. A feed gas stream composed of propene (about 7% by volume, chemical grade), air and inert substances was introduced into the tubular reactor and the propene was converted over the fixed catalyst bed. The amount of propene supplied was chosen such that the quotient of propene gas rate in litres per hour and the catalyst charge used in litres has a value of 146 h$^{-1}$. The propene conversion was adjusted via the choice of bath temperature to a value of 97+/−0.5%. In addition, the air rate for oxidation was adjusted such that, at the propene conversion established, the residual oxygen content in the gas stream after a single pass through the reactor was 6% by volume. For all catalysts, the cumulative yield of acrolein and acrylic acid was always more than 90%, and the yield of acrolein was always at least 84%. In all tests with the catalysts based on the active masses of Examples 2a to 2c and 3a to 3b, the respective maximum temperature in the catalyst fixed bed was determined.

TABLE 1

Overview of the temperatures in the reactions of Example 6.

| Catalyst (from Example) | GHSV [h$^{-1}$] | Propylene [% by vol.] | T$_{bath,reactor}$ [° C.] | T$_{max,reactor}$ [° C.] |
|---|---|---|---|---|
| 2a (inventive) | 2057 | 7.09 | 348 | 422 |
| 2b (inventive) | 2051 | 7.12 | 347 | 422 |
| 2c (inventive) | 2046 | 7.15 | 355 | 419 |
| 3a (comparative example) | 2036 | 7.16 | 352 | 437 |
| 3b (comparative example) | 2025 | 7.21 | 360 | 435 |

Example 7

The catalysts produced in Example 5 from the active masses of Examples 2a to 2c and 3a to 3b were used in the partial gas phase oxidation of propene. For this purpose, a tubular reactor having an internal tube diameter of 20.5 mm was charged in each case with a catalyst fixed bed having a length of 285 cm. The tubular reactor was surrounded by a bath with which the temperature of the fixed catalyst bed and of the reaction mixture flowing through the catalyst fixed bed was regulated. A feed gas stream composed of propene (about 7% by volume, chemical grade), air and inert substances was introduced into the tubular reactor and the propene was converted over the fixed catalyst bed. The amount of propene supplied was chosen such that the quotient of propene gas rate in litres per hour and the catalyst charge used in litres has a value of 153 h$^{-1}$. The propene conversion was adjusted via the choice of bath temperature to a value of 97+/−0.5%. In addition, the air rate for oxidation was adjusted such that, at the propene conversion established, the residual oxygen content in the gas stream after a single pass through the reactor was 6% by volume. For all catalysts, the cumulative yield of acrolein and acrylic acid was always at least 91%, and the yield of acrolein was always at least 84%. In all tests with the catalysts based on the active masses of Examples 2a to 2c and 3a to 3b, the respective maximum temperature in the catalyst fixed bed was determined.

TABLE 2

Overview of the temperatures in the reactions of Example 7.

| Catalyst (from Example) | GHSV [h$^{-1}$] | Propylene [% by vol.] | T$_{bath,reactor}$ [° C.] | T$_{max,reactor}$ [° C.] |
|---|---|---|---|---|
| 2a (inventive) | 2129 | 7.16 | 345 | 422 |
| 2b (inventive) | 2157 | 7.08 | 350 | 422 |
| 2c (inventive) | 2136 | 7.16 | 355 | 419 |
| 3a (comparative example) | 2120 | 7.21 | B 360* | 437 |
| 3b (comparative example) | 2121 | 7.19 | >360 | 435 |

Example 8

The catalysts produced in Example 5 from the active masses of Examples 3a to 3b and 4a to 4b were used in the partial gas phase oxidation of propene. For this purpose, a tubular reactor having an internal tube diameter of 20.5 mm was charged in each case with a catalyst fixed bed having a length of 285 cm. The tubular reactor was surrounded by a bath with which the temperature of the catalyst fixed bed and of the reaction mixture flowing through the catalyst fixed bed was regulated. A feed gas stream composed of propene (about 7% by volume, chemical grade), air and inert substances was introduced into the tubular reactor and the propene was converted over the fixed catalyst bed. The amount of propene supplied was chosen such that the quotient of propene gas rate in litres per hour and the catalyst charge used in litres has a value of 146 h$^{-1}$. The propene conversion was adjusted via the choice of bath temperature to a value of 97+/−0.5%. In addition, the air rate for oxidation was adjusted such that, at the propene conversion established, the residual oxygen content in the gas stream after a single pass through the reactor was 6% by volume. For all catalysts, the cumulative yield of acrolein and acrylic acid was always at least 90%, and the yield of acrolein was always at least 84%. In all tests with the catalysts based on the active masses of Examples 4a to 4b and 3a to 3b, the respective maximum temperature in the catalyst fixed bed was determined.

TABLE 3

Overview of the temperatures in the reactions of Example 8.

| Catalyst (from Example) | GHSV h$^{-1}$ = 50 | Propylene [% by vol.] | T$_{bath,reactor}$ [° C.] | T$_{max,reactor}$ [° C.] |
|---|---|---|---|---|
| 4a (inventive) | 2057 | 7.09 | 354 | 423 |
| 4b (inventive) | 2067 | 7.06 | 357 | 425 |
| 3a (comparative example) | 2036 | 7.16 | 352 | 437 |
| 3b (comparative example) | 2025 | 7.21 | 360 | 435 |

The invention claimed is:

1. A process for producing a mixed oxide catalyst, the process comprising
   a) providing a solution and/or suspension of precursor compounds of components of mixed oxide catalyst, wherein the solution and/or suspension contains a precursor compound of bismuth and a precursor compound of molybdenum or a precursor compound of bismuth and molybdenum, and wherein, when the suspension is subjected to spray-drying, a concentration of solids in the suspension is 10 to 50% by weight,
   b) spray-drying the solution and/or suspension provided in a) in cocurrent together with a gas stream having an entrance temperature into a spray dryer of 160+/−10° C. to 200+/−10° C. and an exit temperature from the spray dryer of 90+/−10° C. to 105+/−10° C., wherein the gas stream has a mean flow velocity in the spray dryer of 2.0+/−0.3 cm/s to 4.5+/−0.3 cm/s, or
   b') spray-drying the solution and/or suspension provided in a) essentially in cocurrent together with a main gas stream having an entrance temperature into the spray dryer of 260+/−10° C. to 300+/−10° C. and an exit temperature from the spiny dryer of 115+/−10° C. to 130+/−10° C., wherein the main gas stream has a mean flow velocity in the spray dryer of 2.0+/−0.3 cm/s to 4.5+/−0.3 cm/s, with feeding of an additional gas stream having an entrance temperature of less than 100° C. and not more than 30° C. into the spray dryer between entrance and exit points of the main gas stream into the spray dryer and from the spray dryer, wherein the additional gas stream has a mean flow velocity of less than 2.0 cm/s, and c) calcining spray particles obtained from b) or b') to yield a catalytic active mass.

2. The process according to claim 1, wherein the process comprises b') in which the additional gas stream is fed in at an angle of 90+/−5° to 0° relative to a wall of the spray dryer upward in an axial direction of the spray dryer.

3. The process according to claim 1, wherein the process comprises b') in which the additional gas stream is fed into the spray dryer at a point between one third and three quarters of a distance between the entrance and exit points for the main gas stream in the spray dryer.

4. The process according to claim 1, wherein a throughput of the solution and/or suspension sprayed into the spray dryer is 1 to 6 kg/h.

5. The process according to claim 1, wherein the solution and/or suspension provided in a) comprises precursor compounds of all components of the mixed oxide catalyst.

6. The process according to claim 1, wherein the solution and/or suspension in a) also contains at least one precursor compound of elements selected from the group consisting of iron, tungsten, phosphorous, cobalt, nickel, alkali metal, alkaline earth metal, cerium, manganese, chromium, vanadium, niobium, selenium, tellurium, gadolinium, lanthanum, yttrium, palladium, platinum, ruthenium, silver, gold, samarium, silicon, aluminum, titanium, and zirconium.

7. The process according to claim 1, wherein solutions and/or suspensions comprising precursor compounds each of different components of the mixed oxide catalyst are used in step a) and steps a) and b) or a) and b') are repeated more than once.

8. The process according to claim 7, further comprising d) mixing the catalytic active masses obtained from c) then solutions and/or suspensions of precursor compounds each of different components of the mixed oxide catalyst are used in b) or b'), to yield a catalytic active mass comprising all the components of the mixed oxide catalyst.

9. The process according to claim 8, further comprising e) adding a shaping agent and/or binder to the catalytic active mass obtained from c) or d), f) shaping the catalytic active mass obtained from e) to obtain a shaped body comprising the mixed oxide catalyst, and g) drying and/or calcining and/or heat-treating the shaped catalyst body obtained from f).

10. The process according to claim 1, further comprising h) providing a washcoat suspension comprising the catalytic active mass obtained from c), i) applying the washcoat suspension from h) to a support material, and j) drying and/or calcining and heat-treating the support material obtained from to yield a supported mixed oxide catalyst.

11. A method for preparing an unsaturated aldehyde and/or acid, the method comprising: partially oxidizing at least one olefin in the presence of a mixed oxide catalyst obtained by the process according to claim 1.

12. The method according to claim 11, wherein the olefin is a $C_1$-$C_4$ olefin.

* * * * *